United States Patent
Casiraro et al.

(10) Patent No.: US 11,969,184 B2
(45) Date of Patent: Apr. 30, 2024

(54) BALLOON CATHETER WITH SELECTIVELY POSITIONABLE SCORING ELEMENT

(71) Applicant: BARD PERIPHERAL VASCULAR, INC., Franklin Lakes, NJ (US)

(72) Inventors: Matt Casiraro, Tempe, AZ (US); Andrzej J. Chanduszko, Chandler, AZ (US)

(73) Assignee: BARD PERIPHERAL VASCULAR, INC., Franklin Lakes, NJ (US)

( * ) Notice: Subject to any disclaimer, the term of this patent is extended or adjusted under 35 U.S.C. 154(b) by 0 days.

(21) Appl. No.: 18/286,372

(22) PCT Filed: Apr. 12, 2021

(86) PCT No.: PCT/US2021/026846
§ 371 (c)(1),
(2) Date: Oct. 11, 2023

(87) PCT Pub. No.: WO2022/220788
PCT Pub. Date: Oct. 20, 2022

(65) Prior Publication Data
US 2024/0081856 A1    Mar. 14, 2024

(51) Int. Cl.
*A61B 17/3207*    (2006.01)
*A61B 17/22*    (2006.01)
*A61M 25/10*    (2013.01)

(52) U.S. Cl.
CPC ............... *A61B 17/320725* (2013.01); *A61B 2017/22039* (2013.01); *A61B 2017/22061* (2013.01); *A61M 2025/109* (2013.01)

(58) Field of Classification Search
CPC ...... A61B 17/32075; A61B 17/320725; A61B 2017/320733; A61B 2017/320741; A61B 2017/22039; A61B 2017/22048; A61B 2017/22051; A61M 2025/109
See application file for complete search history.

(56) References Cited

U.S. PATENT DOCUMENTS

| 7,780,715 | B2 | 8/2010 | Solar et al. |
| 2004/0143287 | A1 | 7/2004 | Konstantino |
| 2011/0152905 | A1 | 6/2011 | Eaton |
| 2014/0324079 | A1 | 10/2014 | Silvestro |

*Primary Examiner* — Ashley L Fishback
(74) *Attorney, Agent, or Firm* — Dickinson Wright PLLC; Andrew D. Dorisio

(57) ABSTRACT

An apparatus is provided for scoring a treatment location in a vessel. A catheter includes an expandable element or inflatable balloon for achieving dilatation. A scoring element includes an elongated scoring wire having at least one ring for selective positioning over the inflatable balloon, which may then be inflated to provide scoring function in both a longitudinal and transverse direction. A plurality of the rings may be provided, and may be adapted for use with a variety of different sizes or lengths of balloons. Related methods are also disclosed.

21 Claims, 3 Drawing Sheets

BALLOON CATHETER WITH SELECTIVELY POSITIONABLE SCORING ELEMENT

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

Dilatation catheters with expandable elements or balloons are often used to treat lesions in vessels. However, difficulties are encountered in navigating tortuous anatomy and safely crossing very tight lesions. Moreover, some lesions are difficult to dilate using just a balloon, and require the application of a focused force, such as provided by a scoring element to dilate the lesion at safe inflation pressures.

U.S. Pat. No. 7,780,715 to Solar et al. describes a system that may be used to provide enhanced force to treat a lesion. This system has a flexible advancement member with a tracking member slidable over a guidewire, and a balloon having a distal end attached to the tracking member. This type of system fixes the location of the scoring elements (wires), which can limit flexibility in certain applications. The scoring elements also extend only longitudinally, and thus do not provide scoring function in a transverse direction, which may be desirable in some applications so as to enhance the scoring/cracking function, especially for highly calcified lesions.

p

SUMMARY OF THE INVENTION

An object of the disclosure is to provide a selectively positionable or repositionable scoring element, potentially with both a longitudinal and a transverse component, and which in any case may be selectively used to provide scoring functionality, when such is desired, including in connection with a wide variety of catheters including expandable elements or balloons to achieve dilatation.

According to a first aspect of the disclosure, an apparatus for providing scoring at a treatment location in a vessel is provided. The apparatus comprises a catheter including an inflatable balloon. A scoring element includes an elongated scoring wire having at least one ring adapted for selective positioning over the inflatable balloon.

In one embodiment, the elongated scoring wire includes a plurality of rings. The plurality of rings may comprise a single wire connected to the elongated scoring wire. Alternatively, each of the plurality of rings may be formed by a single wire connected to the elongated scoring wire.

The plurality of rings may be arranged such that all overlie a barrel portion of the inflatable balloon when inflated. Alternatively, the plurality of rings may be arranged such that at least one ring overlies a barrel portion of the inflatable balloon when inflated and at least one ring does not overlie the barrel portion. One or more of the rings may be angled relative to the elongated scoring wire in a deployed position.

One or more of the rings may include one or more focal pressure points, which may be different in size or type. The catheter may have a length, and a length of the elongated scoring wire may be greater than the length of the catheter.

A sheath or introducer may also be provided, the sheath having a lumen for receiving a portion of the catheter and a portion of the elongated scoring wire when the ring is positioned over the balloon.

According to another aspect of the disclosure, an apparatus for scoring a treatment location in a vessel is provided. The apparatus comprises a catheter including an inflatable balloon and a scoring element for selective positioning over the inflatable balloon. The scoring element includes a longitudinal component for extending along the inflatable balloon for providing longitudinal scoring when the balloon is inflated, as well as a transverse component for providing transverse scoring when the inflatable balloon is inflated.

Yet a further aspect of the disclosure is an apparatus for providing scoring at a treatment location in a vessel. The apparatus comprises a catheter including an inflatable balloon. A scoring element includes an elongated scoring wire and having at least one ring connected to the elongated scoring wire. A guidewire extends through the at least one ring of the elongated scoring wire.

In one embodiment, the elongated scoring wire includes a plurality of rings through which the guidewire extends. The plurality of rings may comprise a single wire connected to the elongated scoring wire. Each of the plurality of rings may be formed by a single wire connected to the elongated scoring wire, or the plurality of rings may be arranged such that all overlie a barrel portion of the inflatable balloon when inflated.

The plurality of rings may be arranged such that at least one ring overlies a barrel portion of the inflatable balloon when inflated and at least one ring does not overlie the barrel section. A second elongated wire may connect the plurality of rings. At least one ring may be angled relative to the elongated scoring wire in a deployed position. The at least one ring may include one or more focal pressure points.

The catheter has a length, and a length of the elongated scoring wire is greater than the length of the catheter. The apparatus may further include a sheath having a lumen for receiving a portion of the catheter and a portion of the elongated scoring wire when the ring is positioned over the inflatable balloon.

Yet another aspect of the disclosure pertains to a method for providing scoring at a treatment location in a vessel. The method comprises positioning a scoring element including at least one collapsed ring in the vessel, moving the at least one ring to a deployed position, inserting an inflatable balloon within the at least one ring when deployed, and inflating the balloon. The method may further comprise the step of passing the catheter and the at least one ring along a guidewire. The method may further comprise providing a portion of the catheter and a portion of the elongated scoring element within a lumen of a sheath when the ring is positioned over the balloon.

BRIEF DESCRIPTION OF THE DRAWINGS

The above and further advantages of the present disclosure may be better understood by referring to the following description in conjunction with the accompanying drawings in which.

Figure 1:
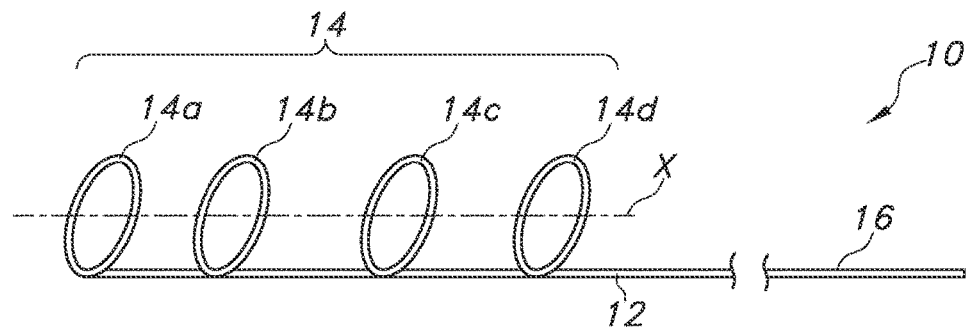
FIG. 1 is side view of a repositionable scoring element according to one aspect of the disclosure.

The dimensions of some of the elements may be exaggerated relative to other elements for clarity or several physical components may be included in one functional block or element. Further, sometimes reference numerals may be repeated among the drawings to indicate corresponding or analogous elements. Moreover, some of the parts depicted in the drawings may be combined into a single function.

DETAILED DESCRIPTION

In the following detailed description, numerous specific details are set forth to provide a thorough understanding of the presently disclosed invention(s). The disclosed embodiments may be practiced without these specific details. In other instances, well-known methods, procedures, components, or structures may not have been described in detail so as not to obscure the present inventive concepts.

The invention is not limited in its application to the details of construction and the arrangement of the components set forth in the following description or illustrated in the drawings. The inventive concepts disclosed are capable of other embodiments or of being practiced or carried out in various ways. Also, it is to be understood that the phraseology and terminology employed herein are for the purpose of description and should not be regarded as limiting.

Certain features of the disclosed embodiments that are, for clarity, described in the context of separate embodiments, may also be provided in combination in a single embodiment. Conversely, various features of the invention that are, for brevity, described in the context of a single embodiment, may also be provided separately or in any suitable sub-combination.

With reference to FIG. 1, a scorer or scoring element 10 according to a first aspect of the disclosure is shown. The scoring element 10 is adapted for providing a scoring capability in a longitudinal direction, as well as in a transverse direction. Specifically, the scoring element 10 includes a longitudinal component, such as in the form of an elongated wire 12, and a transverse component, such as by fixing one or more selectively deployable rings 14 along a distal end portion of the wire. Consequently, as outlined further in the description that follows, when deployed in a vessel in connection with an expandable element, such as an inflatable balloon, the scoring element 10 may provide both longitudinal and transverse scoring capabilities.

The rings 14 may take the form of generally circular, closed bands of material (wire) directly connected along the circumference or periphery to the elongated wire 12 of the scoring element 10. Four rings 14a, 14b, 14c, 14d are shown on the elongated wire 12 forming the scoring element 10 shown in in FIG. 1, but fewer or more may be provided depending on the desired application. The number and size of the rings 14 provided depends, in part, on the size or length of the balloon or the desired treatment to be provided, but would generally correspond in number to the length of a working surface of a balloon and in size to a diameter of the working surface of the balloon. The scoring element 10 also includes a proximal portion 16, and may be of a sufficient length to locate the scoring elements, such as rings 14, at a desired treatment location within the vasculature from outside the associated body.

The rings 14 may be directly and permanently attached to the scoring element 10, such as by welding or other mechanical connection between the circular bands of material and the material of the wire, as outlined further in the following description. The arrangement is such that the rings 14 have an erected or deployed position, as shown in FIG. 1, in alignment with a central axis X passing therethrough. The rings 14 when deployed are generally upright, but may extend at an angle relative to a vertical axis transverse to the central axis X (e.g., tilted in a proximal direction, or towards the proximal portion 16 of wire 12, such that an apex of the ring 14 and a point of connection to the wire 12 lie in different vertical planes; e.g., an acute angle, such as from greater than zero to less than 90 degrees from the horizontal, more specifically, from about 30-60 degrees, and still more specifically, about 45 degrees).

As a result of the manner of connection and the resulting flexibility, the rings 14 may also collapse relative to the associated wire 12, such as by collapsing or folding toward the wire. Alternatively, the rings 14 may achieve the erect position by spring-like action to move from a collapsed to an erected (transverse) position relative to the wire. This relative movement may be achieved using mechanical force or by way of a shape memory material, such as Nitinol). When multiple rings 14 are present, the spacing of the rings 14 along the distal portion of the wire 12 is such that the rings may collapse without contacting each other, which is desirable to avoid interference in achieving the erect state. However, it is possible for the rings 14 to partially overlap and/or contact each other in the collapsed or retracted position.

Figure 2A:
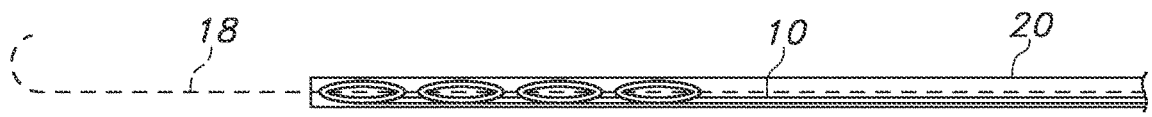
FIGS. 2A, 2B, and 2C are progressive views illustrating a use of the scoring element of FIG. 1.
Figure 2B:
Figure 2C:
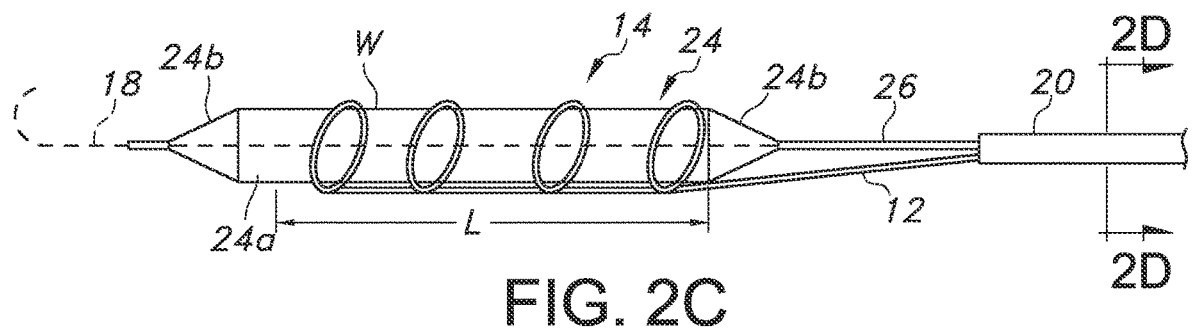

An exemplary use of the scoring element 10 is shown in FIGS. 2A, 2B, and 2C. As shown in FIG. 2A, a guidewire 18 may be pre-positioned in a vessel in need of treatment. A sheath 20 may then be advanced along the guidewire 18, such as through a lumen 22. The scoring element 10 may be passed along the guidewire 18, extending through the rings 14 (which are closed and thus capture and travel along the guidewire 18 in a captured state) in a collapsed or retracted condition as shown in FIG. 2A.

Figure 2D:
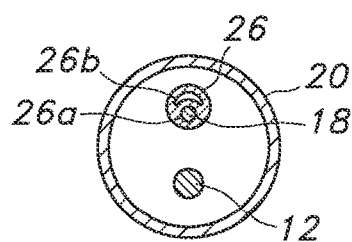
FIG. 2D is a cross-sectional view taken along line 2D-2D of FIG. 2C.

As shown in FIG. 2B, the scoring element 10 may be advanced from a distal end of the sheath 20 to a desired treatment location. The rings 14 may then be deployed, as shown, remaining captive on the guidewire 18 at all times in view of the enclosed nature of the rings. An expandable element, such as a balloon 24 in a deflated condition associated with a catheter 26, may then be advanced through the sheath 20 along the guidewire 18 (such as through a guidewire lumen 26a, as shown in FIG. 2D) so as to pass through the ring(s) 14 (the balloon 24 is shown as being transparent to illustrate the concept).

Once the deflated balloon 24 is positioned within the rings 14, such as along a generally cylindrical, or "barrel," portion 24a between tapered end portions 24b, the balloon 24 may then be inflated (such as via an inflation lumen 26b associated with catheter 26) within the rings 14. Consequently, the rings 14 are urged outwardly in a radial direction relative to axis X, and thus form raised scoring elements useful for providing scoring functionality to a lesion. As can be appreciated, this scoring may be achieved simultaneously in both a transverse direction as a consequence of the circumferential nature of the rings 14 extending around the barrel portion of the balloon, as well as in a longitudinal direction as a consequence of the associated elongated wire 12 extending generally linearly along this same portion of the balloon (see line L in FIG. 2C along the balloon working surface W of the barrel portion 24a).

Once the desired scoring operation is completed, the balloon 24 may be deflated. The balloon 24 in the deflated state may then be repositioned along with the rings 14 (possibly once retracted into sheath 20) to another location in need of treatment by scoring. Alternatively, the balloon 24 and scoring element 10 may simply be withdrawn from the vasculature via sheath 20.

Figure 3:
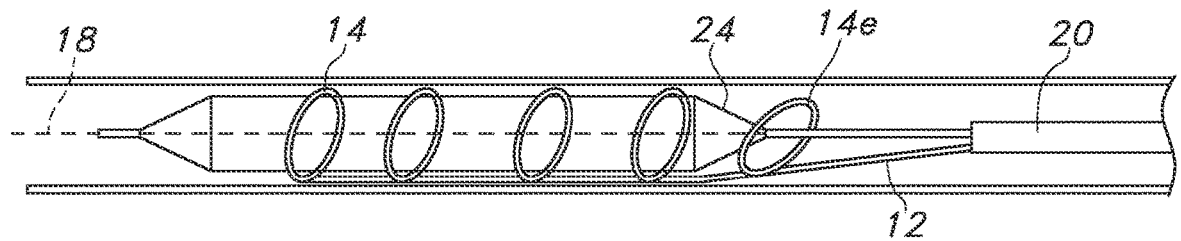
FIGS. 3, 4, and 5 are alternative embodiments.

As can be appreciated, the arrangement shown in FIG. 2 provides a relatively small ring to balloon length ratio (that is, the number of rings for a given length of balloon). FIG. 3 illustrates a larger ring to balloon length ratio with the same scoring element. As noted above, the rings 14 may be angled for use in a smaller vessel and may be made increasingly planar as the vessel increases in size (since further movement in the radial direction during erection would be possible).

Additionally, when multiple rings are present, only some of the rings 14 may be engaged with the balloon 24 during the procedure minimizing the need to match exactly the balloon length to the scoring element length/number of rings. For example, it can also be understood from FIG. 3 that not all rings 14 may overlie the barrel portion 24a of the balloon 24. For example, the proximal ring 14d in this illustration overlies the proximal cone portion 24b of the balloon 24, which is of sufficiently small diameter so as to not engage or erect the ring 14d on balloon inflation. This allows for use of the scoring element 10, even when the ring boundaries (that is, the distance from the proximal ring to the distal ring) do not match the length of the barrel portion 24a, and thus further expands the usability.

It is estimated that two sizes of scoring rings 14 may cover eight different balloon diameters. This would reduce the number of different types of scoring elements 10 needed to be kept on hand. While the rings 14 may be sized to have an inner diameter slightly greater than that of the balloon 24, it is also possible to undersize the rings. This would produce pillowing effect on the balloon (not shown). The various sizing options delivered by a single device would give physicians more flexibility to effectively treat diverse lesions, and thus potentially reduce costs and enhance treatment outcomes.

Figure 4:
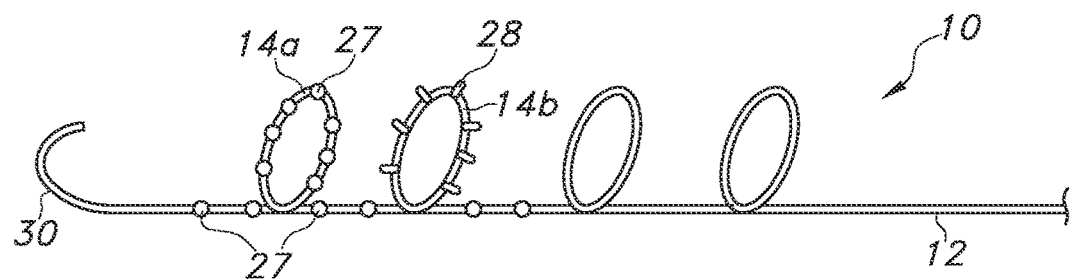

The rings 14 of the scoring element 10 may optionally be provided with enhanced scoring capabilities, such as by providing the ring(s) 14 with structure for achieving focal pressure points. For example, as shown in FIG. 4, the distal ring 14a is shown as including focused force elements in the form of protrusions, such as rounded or spherical beads 27 integrally formed with the material. These beads 27 may enhance the scoring or cutting effect provided when pressed into a lesion. Additionally, or alternatively, the focused force elements, such as one or more beads 27, may also be selectively provided along the wire 12. Another example is shown in connection with next-proximal ring 14b, which includes outwardly directed spikes 28 as the focused force elements. Combinations of these approaches may be provided on the same or different rings in any desired position, and each ring may include a different type of enhancement, which is again optional.

The scoring element 10 of FIG. 4, and wire 12 in particular, is also shown as having a guidewire tip 30, such as a curving or hooked end. This arrangement may be used to aid in locating the wire within the vasculature. In this case, the wire 12 is also longer than the catheter 26 (including balloon 24).

Figure 5:
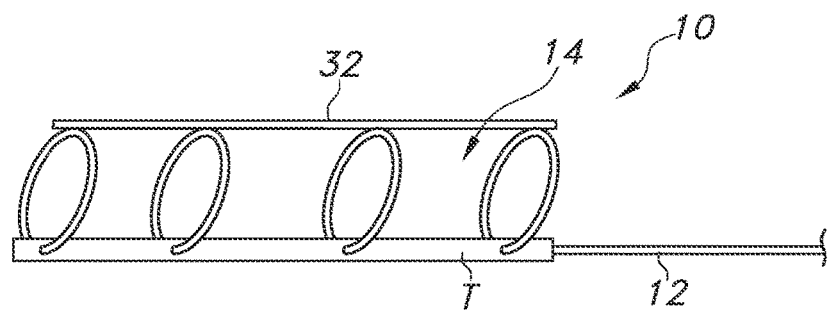

FIG. 5 shows a scoring element 10 arrangement similar to FIG. 1. However, the rings 14 may be further connected to a second elongated wire 32. This second elongated wire 32 may be substantially shorter than wire 12 (such as having a length corresponding to the spacing of the proximal and distal rings). This shorter wire 32 may also be connected at a different location (such as to the opposite end of the ring). This arrangement may lend stability to the arrangement, without negatively impacting collapsibility, and also provides added longitudinal as well as transverse/angled tissue scoring, which may enhance lesion cracking/dilation. A plurality of such wires 32 may be provided spaced in the circumferential direction around the ring 14.

Further illustrated in FIG. 5 is an alternative manner of assembly of the wire 12 and ring(s) 14. The connection may be established by a heat shrink tubing T applied over a distal portion of the wire 12 and through which the ring(s) 14 partially pass. When shrunk, the tubing T thus serves to connect the rings 14 to the wire 12, while achieving the desired flexibility to allow for collapse for loading into sheath 20 and then erection when deployed for receiving a balloon 25. The second wire 32 is entirely optional, as previously noted.

Figure 6:
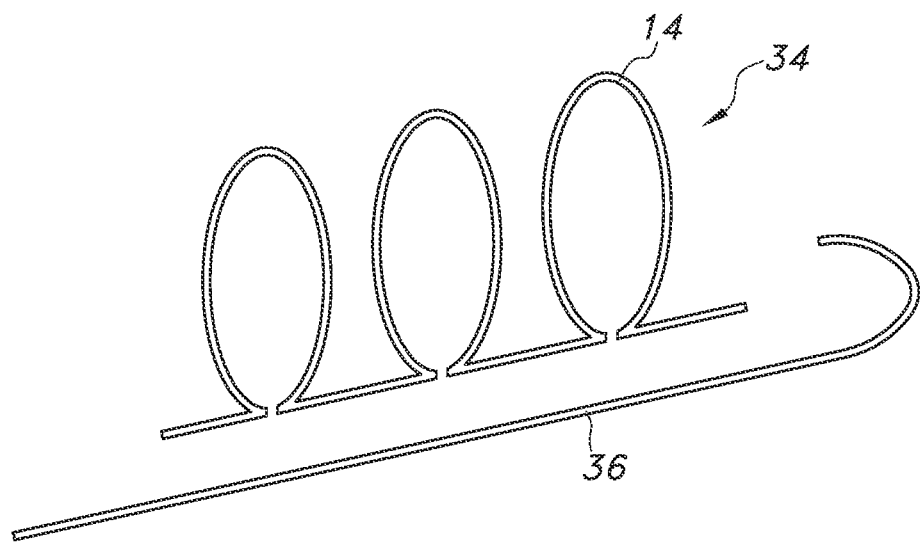
FIGS. 6 and 6A illustrate one example of a manner for assembling a scoring element with rings.
Figure 6A:
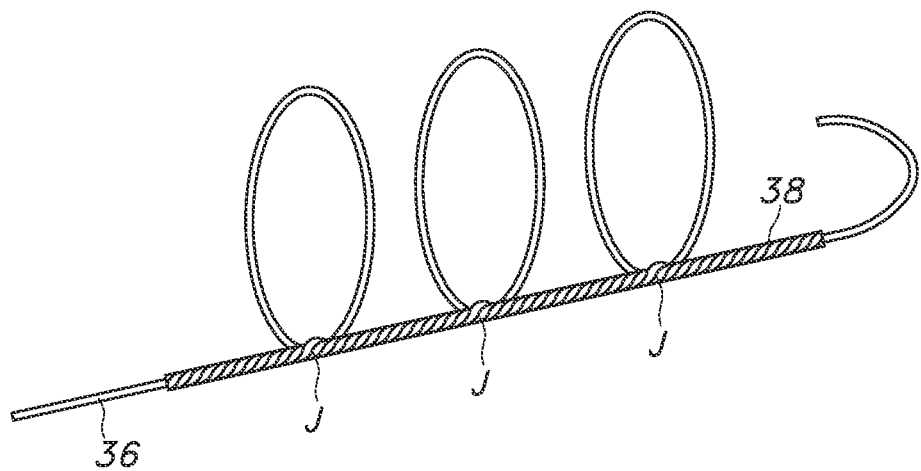

Turning to FIGS. 6 and 6A, an example of fabrication of the scoring element 10 is shown. The manufacturing process may be involve providing or forming a single wire 34 with partially open rings 14 from a single strand, such as by using heat setting, mandrel forming, or the like. A longer base wire 36 may be cut to length separately and connected to the single wire 34 including the rings 14. For example, a small diameter wire 38 could then be wrapped around the base wire 36 and connecting the rings 14 and thus forming a joint J at each juncture between the rings 14 and the base wire 36. Additionally, small laser spot weld(s) may be used to reinforce as needed at locations where the coiled wire 38 is wrapped, including at the joints J. The ring(s) 14 may also be separately formed as discrete structures, and then simply attached to an elongated wire, such as by welding as previously noted or other forms of attachment. Furthermore, the ring(s) may each be formed of multiple wires, such as segments of interconnected wires to form a ring or multiple interconnected rings.

Figure 7:
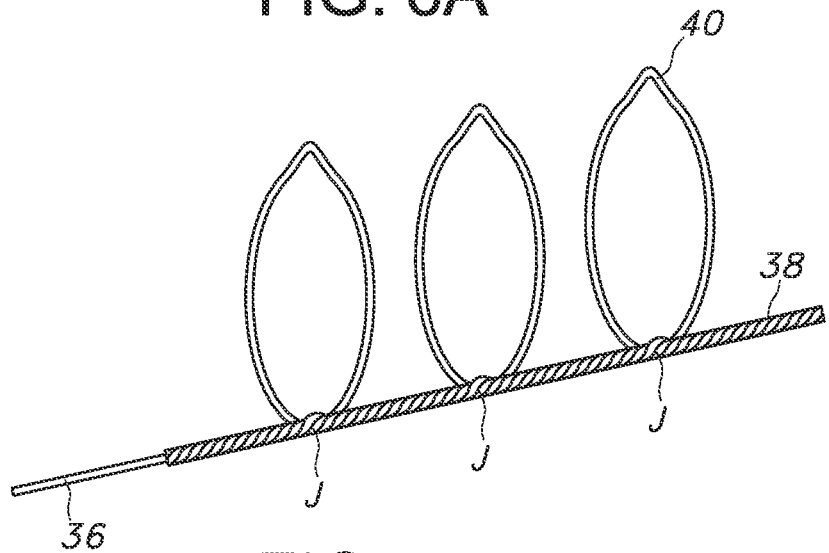
FIG. 7 illustrates an alternative embodiment.

FIG. 7 also illustrates that one or more of the rings 14 may be provided with a relief structure for establishing preferential folding, such as a notch 40. The notch 40 may be provided a portion opposite the point of connection to the wire 12, such as the joint J. This notch 40 may aid in the collapse or folding of the ring 14 when desired, and hence may facilitate loading the wire 10 into the sheath 20. More than one such notch 40 may be provided as desired for a particular application, and may disappear when the ring is erected, or may provide additional focused force if not disappeared on erection.

As noted above, the scoring element 10 may be fabricated all or partially of a shape memory material, such as Nitinol. The scoring element 10 may also be formed of stainless steel. Similar metallic material, such as those used for endovascular snares and guidewires, may also be used, without limitation.

In summary, a repositionable scoring element 10 providing multi-dimensional scoring capabilities may be used in connection with a variety of catheters having different sizes of inflatable balloons. This arrangement allows clinicians to use a chosen balloon without regard to any existing scoring capability provided. The scoring element 10 includes one or more ring(s) 14, which may be oversized relative to a balloon for scoring, or undersized for scoring using the balloon itself. The scoring element 10 is readily adaptable to fit a broad range of balloon diameters and lengths. The arrangement may achieve longitudinal as well as transverse/angled tissue scoring which enhances lesion cracking/dilation. The scoring element 10 would also be low cost to manufacture, and would provide a low-profile arrangement that may be easily delivered and deployed at a treatment location using existing technologies.

Summarizing, this disclosure may be considered to relate to the following items:

1. An apparatus for providing scoring at a treatment location in a vessel, comprising:
   a catheter including an inflatable balloon; and
   a scoring element comprising an elongated scoring wire having at least one ring adapted for selective positioning over the inflatable balloon.
2. The apparatus of item 1, wherein the elongated scoring wire includes a plurality of rings.
3. The apparatus of item 1 or item 2, wherein the ring(s) comprise a single wire connected to the elongated scoring wire.
4. The apparatus of item 1 or item 2, wherein the ring(s) are formed by a single wire connected to the elongated scoring wire.
5. The apparatus of any of items 2-4, wherein the plurality of rings are arranged such that all overlie a barrel portion of the inflatable balloon when inflated.
6. The apparatus of any of items 2-4, wherein the plurality of rings are arranged such that at least one ring overlies a barrel portion of the inflatable balloon when inflated and at least one ring does not overlie the barrel portion.
7. The apparatus of any of items 1-6, wherein the ring(s) are angled relative to the elongated scoring wire in a deployed position.
8. The apparatus of any of items 1-7, wherein the ring(s) or elongated scoring wire include one or more focal pressure points.
9. The apparatus of any of items 1-8, wherein the catheter has a length, and a length of the elongated scoring wire is greater than a length of the catheter.
10. The apparatus of any of items 1-9, further including a sheath having a lumen for receiving a portion of the catheter and a portion of the elongated scoring wire when the ring(s) are positioned over the balloon.
11. An apparatus for scoring a treatment location in a vessel, comprising:
    a catheter including an inflatable balloon; and
    a scoring element for selective positioning over the inflatable balloon, the scoring element including a longitudinal component for extending along the inflatable balloon for providing longitudinal scoring when the balloon is inflated and a transverse component for providing transverse scoring when the inflatable balloon is inflated.
12. An apparatus for providing scoring at a treatment location in a vessel, comprising:
    a catheter including an inflatable balloon;
    a scoring element including an elongated scoring wire and having at least one ring connected to the elongated scoring wire; and
    a guidewire extending through the at least one ring of the elongated scoring wire.
13. The apparatus of item 12, wherein the elongated scoring wire includes a plurality of rings through which the guidewire extends.
14. The apparatus of item 12 or item 13, wherein the ring(s) comprise a single wire connected to the elongated scoring wire.
15. The apparatus of item 12 or item 13, wherein the ring(s) are formed by a single wire connected to the elongated scoring wire.
16. The apparatus of any of items 13-15, wherein the plurality of rings are arranged such that all overlie a barrel portion of the inflatable balloon when inflated.
17. The apparatus of any of items 13-15, wherein the plurality of rings are arranged such that at least one ring overlies a barrel portion of the inflatable balloon when inflated and at least one ring does not overlie the barrel section.
18. The apparatus of any of items 12-17, further including a second elongated wire connecting the plurality of rings.
19. The apparatus of any of items 12-18, wherein the ring(s) are angled relative to the elongated scoring wire in a deployed position.
20. The apparatus of any of items 12-19, wherein the ring(s) or elongated scoring wire include one or more focal pressure points.
21. The apparatus of any of claims 12-20, wherein the catheter has a length, and a length of the elongated scoring wire is greater than the length of the catheter.
22. The apparatus of any of claims 12-21, further including a sheath having a lumen for receiving a portion of the catheter and a portion of the elongated scoring wire when the ring is positioned over the inflatable balloon.
23. A method for providing scoring at a treatment location in a vessel, comprising: positioning a scoring element including at least one collapsed ring in the vessel; moving the at least one ring to a deployed position; and inserting an inflatable balloon within the at least one ring when deployed; and inflating the balloon.
24. The method of item 23, further including the step of passing the catheter and the at least one ring along a guidewire.
25. The method of item 22 or item 23, further including a sheath having a lumen, and providing a portion of the catheter and a portion of the elongated scoring element within the sheath when the ring is positioned over the balloon.

Although the invention has been described in conjunction with specific embodiments, many alternatives, modifications, and variations will be apparent to those skilled in the art. Accordingly, it embraces all such alternatives, modifications, and variations that fall within the spirit and scope of the appended claims. For example, the longitudinal scoring capability afforded by scoring element 10 could be eliminated or minimized, if desired, by attaching the wire 12 along an inner circumference of the rings 14, or otherwise shaping the wire 12 in a particular manner to minimize the contact with a lesion on expansion of the balloon 24. It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment may also be illustratively described and presented in the context or format of a plurality of separate embodiments.

All publications, patents and patent applications mentioned in this specification are herein incorporated in their entirety by reference into the specification, to the same extent as if each individual publication, patent or patent application was specifically and individually indicated to be incorporated herein by reference. In addition, the citation or identification of any reference in this application shall not be construed as an admission that such reference is avail-able as prior art to the present disclosure.

The invention claimed is:

1. An apparatus for providing scoring at a treatment location in a vessel, comprising:
    a catheter including an inflatable balloon; and
    a scoring element comprising an elongated scoring wire attached to at least one ring adapted for selective positioning over the inflatable balloon,
    wherein the catheter has a length, and a length of the elongated scoring wire is greater than the length of the catheter.

2. The apparatus of claim 1, wherein the elongated scoring wire includes a plurality of rings.

3. The apparatus of claim 2, wherein the plurality of rings comprise a single wire connected to the elongated scoring wire.

4. The apparatus of claim 2, wherein each of the plurality of rings is formed by a single wire connected to the elongated scoring wire.

5. The apparatus of claim 2, wherein the plurality of rings are arranged such that all overlie a barrel portion of the inflatable balloon when inflated.

6. The apparatus of claim 2, wherein the plurality of rings are arranged such that at least one ring overlies a barrel portion of the inflatable balloon when inflated and at least one ring does not overlie the barrel portion.

7. The apparatus of claim 1, wherein the at least one ring is angled relative to the elongated scoring wire in a deployed position.

8. The apparatus of claim 1, wherein the at least one ring or the elongated scoring wire includes one or more focal pressure points.

9. The apparatus of claim 1, wherein the at least one ring comprises a generally circular, closed band of material.

10. The apparatus of claim 1, further including a sheath having a lumen for receiving a portion of the catheter and a portion of the elongated scoring wire when the ring is positioned over the balloon.

11. An apparatus for providing scoring at a treatment location in a vessel, comprising:
    a catheter including an inflatable balloon;
    a scoring element including an elongated scoring wire and having at least one ring attached to the elongated scoring wire along a length thereof; and
    a guidewire extending through the at least one ring of the elongated scoring wire,
    wherein the catheter has a length, and the length of the elongated scoring wire is greater than the length of the catheter.

12. The apparatus of claim 11, wherein the elongated scoring wire includes a plurality of rings through which the guidewire extends.

13. The apparatus of claim 12, wherein the plurality of rings comprise a single wire connected to the elongated scoring wire.

14. The apparatus of claim 12, wherein each of the plurality of rings is formed by a single wire connected to the elongated scoring wire.

15. The apparatus of claim 12, wherein the plurality of rings are arranged such that all overlie a barrel portion of the inflatable balloon when inflated.

16. The apparatus of claim 12, wherein the plurality of rings are arranged such that at least one ring overlies a barrel portion of the inflatable balloon when inflated and at least one ring does not overlie the barrel section.

17. The apparatus of claim 12, further including a second elongated wire connecting the plurality of rings.

18. The apparatus of claim 11, wherein the at least one ring is angled relative to the elongated scoring wire in a deployed position.

19. The apparatus of claim 11, wherein the at least one ring or the elongated scoring wire includes one or more focal pressure points.

20. The apparatus of claim 11, wherein the at least one ring comprises a generally circular, closed band of material.

21. The apparatus of claim 11, further including a sheath having a lumen for receiving a portion of the catheter and a portion of the elongated scoring wire when the ring is positioned over the inflatable balloon.

* * * * *